US009688664B2

(12) United States Patent
Keith et al.

(10) Patent No.: US 9,688,664 B2
(45) Date of Patent: *Jun. 27, 2017

(54) MODULATORS OF FATTY ACID AMIDE HYDROLASE

(71) Applicant: JANSSEN PHARMACEUTICA NV, Beerse (BE)

(72) Inventors: John M. Keith, San Diego, CA (US); Jing Liu, San Diego, CA (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

This patent is subject to a terminal disclaimer.

(21) Appl. No.: 14/565,535

(22) Filed: Dec. 10, 2014

(65) Prior Publication Data
US 2015/0099761 A1 Apr. 9, 2015

Related U.S. Application Data

(63) Continuation of application No. 13/695,855, filed as application No. PCT/US2011/034755 on May 2, 2011, now Pat. No. 8,940,745.

(60) Provisional application No. 61/330,522, filed on May 3, 2010.

(51) Int. Cl.
*C07D 405/12* (2006.01)
*A61K 31/496* (2006.01)

(52) U.S. Cl.
CPC ................... *C07D 405/12* (2013.01)

(58) Field of Classification Search
None
See application file for complete search history.

(56) References Cited

U.S. PATENT DOCUMENTS

| | | | |
|---|---|---|---|
| 3,813,395 A | 5/1974 | Nakanishi et al. | |
| 5,780,472 A | 7/1998 | Cho et al. | |
| 6,096,784 A | 8/2000 | Lerner et al. | |
| 6,100,279 A | 8/2000 | Vaccaro et al. | |
| 6,124,299 A | 9/2000 | Baindur et al. | |
| 6,306,959 B1 | 10/2001 | Bolton et al. | |
| 6,387,900 B1 | 5/2002 | Pevarello et al. | |
| 6,395,740 B1 | 5/2002 | Baindur et al. | |
| 6,462,054 B1 | 10/2002 | Boger | |
| 6,881,741 B2 | 4/2005 | Chan Chun Kong et al. | |
| 7,598,249 B2 | 10/2009 | Apodaca et al. | |
| 8,114,866 B2 | 2/2012 | Abouabdellah et al. | |
| 2003/0149036 A1 | 8/2003 | Flohr et al. | |
| 2003/0187040 A1 | 10/2003 | Pevarello et al. | |
| 2004/0220191 A1 | 11/2004 | Schwink et al. | |
| 2006/0014830 A1 | 1/2006 | Abouabdella et al. | |
| 2006/0089344 A1 | 4/2006 | Abouabdelah et al. | |
| 2006/0173184 A1 | 8/2006 | Apodaca et al. | |
| 2006/0178399 A1 | 8/2006 | Nishizawa et al. | |
| 2007/0004741 A1 | 1/2007 | Apodaca et al. | |
| 2007/0270433 A1 | 11/2007 | Brinkman et al. | |
| 2009/0062294 A1 | 3/2009 | Apodaca et al. | |
| 2009/0163508 A1 | 6/2009 | Kori et al. | |
| 2010/0004261 A1 | 1/2010 | Apodaca et al. | |
| 2011/0172230 A1 | 7/2011 | Ishii et al. | |

FOREIGN PATENT DOCUMENTS

| | | |
|---|---|---|
| CN | 1145620 A | 3/1997 |
| DE | 2123784 | 12/1971 |
| EP | 0285219 | 3/1988 |
| JP | 48010160 | 3/1973 |
| JP | S48-10160 | 3/1973 |
| JP | 55015456 | 2/1980 |
| JP | 51176495 | 7/1996 |
| JP | 11139969 | 5/1999 |
| JP | 2000511949 | 9/2000 |
| JP | 2000513009 | 10/2000 |
| JP | 2007-519628 | 7/2007 |
| WO | WO9300342 | 1/1993 |
| WO | WO9609817 | 4/1996 |
| WO | WO9621648 | 7/1996 |
| WO | WO9723458 | 4/1997 |
| WO | WO9742230 | 11/1997 |
| WO | WO9749667 | 12/1997 |
| WO | WO9837077 | 8/1998 |
| WO | WO9924421 | 5/1999 |
| WO | WO9926584 | 6/1999 |

(Continued)

OTHER PUBLICATIONS

Fox et al. Expert Opin.Investig.Drugs, vol. 14, p. 695-703 (2005).*
Teare et al.Expert Opin.Investig.Drugs, vol. 14, p. 859-869 (2005).*
Cravatt et al. Current Opinion in Chemical Biology, vol. 7, p. 469-475 (2003).*
Hill et al. Biology of Mood & Anxiety Disorders 3:19, pp. 1-14 (2013).*
FierceBioTech Drug Development Forum, R&D Report by Damian Garde (Jan. 20, 2016) retrieved from the Internet at http://www.fiercebiotech.com/r-d/j-j-halts-a-depression-program-shadow-of- . . . Jul. 7, 2016.*

(Continued)

*Primary Examiner* — Emily Bernhardt
(74) *Attorney, Agent, or Firm* — Thomas J. Dodd

(57) ABSTRACT

4-(2,2-Difluoro-benzo[1,3]dioxol-5-ylmethyl)-piperazine-1-carboxylic acid (4-chloro-pyridin-3-yl)-amide is described, which is useful as a FAAH modulator. 4-(2,2-Difluoro-benzo[1,3]dioxol-5-ylmethyl)-piperazine-1-carboxylic acid (4-chloro-pyridin-3-yl)-amide may be used in pharmaceutical compositions and methods for the treatment of disease states, disorders, and conditions mediated by fatty acid amide hydrolase (FAAH) activity, such as anxiety, pain, inflammation, sleep disorders, eating disorders, energy metabolism disorders, and movement disorders (e.g., multiple sclerosis). A method of synthesizing 4-(2,2-difluoro-benzo[1,3]dioxol-5-ylmethyl)-piperazine-1-carboxylic acid (4-chloro-pyridin-3-yl)-amide is also disclosed.

9 Claims, No Drawings

(56) References Cited

FOREIGN PATENT DOCUMENTS

| WO | WO9942107 | 8/1999 |
|---|---|---|
| WO | WO9950247 | 10/1999 |
| WO | WO0026203 | 5/2000 |
| WO | WO0105763 | 1/2001 |
| WO | WO0136386 | 5/2001 |
| WO | WO0208221 | 1/2002 |
| WO | WO0240466 | 5/2002 |
| WO | WO02087569 | 11/2002 |
| WO | WO03037271 | 5/2003 |
| WO | WO 03/049741 A1 | 6/2003 |
| WO | WO03047569 | 6/2003 |
| WO | WO03494741 | 6/2003 |
| WO | WO03065989 | 8/2003 |
| WO | WO2004018428 | 3/2004 |
| WO | WO2004033652 | 4/2004 |
| WO | WO 2004/067498 A1 | 8/2004 |
| WO | WO 2004/072025 A2 | 8/2004 |
| WO | WO2004067498 | 8/2004 |
| WO | WO2004072025 | 8/2004 |
| WO | WO2004080966 | 9/2004 |
| WO | WO2004087569 | 10/2004 |
| WO | WO 2004/099176 A1 | 11/2004 |
| WO | WO2004099176 | 11/2004 |
| WO | WO2004110451 | 12/2004 |
| WO | WO2005033652 | 4/2005 |
| WO | WO2006014136 | 2/2006 |
| WO | WO2006074025 | 7/2006 |
| WO | WO2006085108 | 8/2006 |
| WO | WO2007134958 | 8/2007 |
| WO | WO2007096251 | 11/2007 |
| WO | WO 2008-023720 | 2/2008 |
| WO | WO2008023720 | 2/2008 |
| WO | WO2008024139 | 2/2008 |
| WO | WO2008047229 | 4/2008 |
| WO | WO2008153752 | 12/2008 |
| WO | WO 2009/048101 A1 | 4/2009 |
| WO | WO2010/068452 | 6/2010 |
| WO | WO2010/068453 | 6/2010 |

OTHER PUBLICATIONS

FDA report available at http://www.fda.gov/Drugs/DrugSafety/ucm482740.htm (cited by applicant) downloaded on Oct. 22, 2016 (2 pages).*
U.S. Appl. No. 12/557,650, filed Dec. 28, 2011, Janssen Pharmaceutica NV.
U.S. Appl. No. 61/263,477, filed Nov. 23, 2009, Janssen Pharmaceutica NV.
U.S. Appl. No. 61/184,606, filed Jun. 5, 2009, Janssen Pharmaceutica NV.
Ahn K., et al., "Discovery and Characterization of Highly Selective FAAH Inhibitor That Reduces Inflammatory Pain", (Apr. 24, 2009) Chemistry and Biology, Current Biology, London GB, vol. 16(4) pp. 411-420.
Bagshawe et al "Antibody-Directed Enzyme Product Therapy: A Review" Drug Development Research 1995 vol. 34 pp. 220-230.
Baker et al., "Cannabinoids Controls Spasticity and Tremor in a Multiple Sclerosis Model," Nature 2000, 404, 84-87.
Baker et al., "Endocannabinoids Control Spasticity in a Multiple Sclerosis Model," FASEB J. 2001, 15(2), 300-302.
Baker et al., "The Therapeutic Potential of Cannabis in Multiple Sclerosis," Expert Opin Investig Drugs. 2003, 12, 561-567.
Barann et al., "Direct Inhibition by Cannabinoids of Human 5-HT3A Receptors: Probable Involvement of an Allosteric Modulatory Site," Br J Pharmacol. 2002, 137, 589-596.
Berge et al "Pharmaceutical Salts" Journal of Pharmaceutical Sciences 1977 vol. 66(1) pp. 1-19.
Bertolini et al "A New Rational Hypothesis for the Pharmacophore of the Active Metabolite of Leflunomide, A Potent Immunosuppressive Drug" J Med Chem 1997 vol. 40 pp. 2011-2016.
Bisogno et al., "Fatty Acid Amide Hydrolase, An Enzyme With Many Bioactive Substrates. Possible Therapeutic Implications," Curr Pharm Des. 2002, 8, 533-47.
Bodor et al "Novel Approaches to the Design of Safer Drugs: Soft Drugs and Site-Specific Chemical Delivery Systems" Advances in Drug Research 1984 vol. 13 pp. 255-331.
Boger et al "Exceptionally Potent Inhibitors of Fatty Acid Amide Hydrolase: The Enzyme Responsible for Degradation of Endogenous Oleamide and Anandamide" Proc Natl Acad Sci USA 2000 vol. 97(10) pp. 5044-5049.
Boger et al., "Oleamide: An Endogenous Sleep-Inducing Lipid and Prototypical Member of a New Class of Biological Signaling Molecules," Curr Pharm Des. 1998, 4, 303-314.
Boger et al., "Trifluoromethyl Ketone Inhibitors of Fatty Acid Amide Hydrolase: A Probe of Structural and Conformational Features Contributing to Inhibition," Bioorg. Med. Chem. Lett. 1999, 9, 265-270.
Boger et al., "A-Keto Heterocycle Inhibitors of Fatty Acid Amide Hydrolase: Carbonyl Group Modification and A-Substitution," Bioorg. Med. Chem. Lett. 2001, 11, 1517-1520.
Bouaboula et al "Anandamide Induced PPAR'Y Transcriptional Activation and 3T3-LI Preadipocyte Differentiation" Eu J of Pharmacology 2005 vol. 517 pp. 174-181.
Bracey et al., "Structural Adaptations in a Membrane Enzyme That Terminates Endocannabinoid Signaling," Science 2002, 298, 1793-96.
Bundgaard et al, Design of Prodrugs, H. Bundgaard ,Elsevier Press1985 Introduction p. 1.
Cravatt et al, "Molecular Characterization of an Enzyme That Degrades Neuromodulator Fatty-Acid Amides" Nature 1986 vol. 384 pp. 83-87.
Cravatt et al "Chemical Characterization of a Family of Brain Lipids That Induce Sleep" Science 1995 vol. 268 pp. 1506-1509.
Cravatt et al "Supersentitiviy to Anandamide and Enhanced Endogenous Cannabinoid Signaling in Mice Lacking Fatty Acid Amide Hydrolase" Proc Natl Acad Sci USA 2001 vol. 98 (16) pp. 9371-9376.
Croxford et al "Cannabinoid-Mediated Neuroprotection, Not Immunosuppression, May Be More Relevant to Multiple Sclerosis" J Neuroimmunol 2008 vol. 193 pp. 120-129.
Devane et al "Isolation and Structure of a Brain Constituent That Binds to the Cannabinoid Receptor" Science 1992 vol. 258 pp. 1946-1949.
Dinh et al., "Brain Monoglyceride Lipase Participating in Endocannabinoid Inactivation," PNAS, 2002, 99, 10819-24.
Fleisher et al "Improved Oral Drug Delivery: Solubility Limitations Overcome by the Use of Prodrugs" Adv Drug Delivery Rev 1996 vol. 19 pp. 115-140.
Fowler et al., "Fatty Acid Amide Hydrolase: Biochemistry, Pharmacology, and Therapeutic Possibilities for an Enzyme Hydrolyzing Anandamide, 2-Arachidonoylglycerol; Palmitoylethanolamide, and Oleamide," Biochem Pharmacol. 2001, 62, 517-26.
Giang et al., "Molecular Characterization of Human and Mouse Fatty Acid Amide Hydrolases," PNAS 1997, 94, 2238-42.
Gobbi et al "Antidepressant-Like Activity and Modulation of Brain Monoaminergic Transmission by Blockade of Anandamide Hydrolysis" Proc Natl Acad Sci USA 2005 vol. 102(51) pp. 18620-18625.
Goya et al "Recent Advances in Cannabinoid Receptor Agonists and Antagonists" Exp Opin Ther Patents 2000 vol. 10(10) pp. 1529-1538.
Greene et al Protective Groups in Organic Synthesis T.W. Greene and P.G.M. Wuts 3rd Ed John Wiley and Sons 1999 Index.
Handbook of Pharmaceutical Excipients 2009 6th Ed Ed. Raymond C. Rowe Pharmaceutical Press.
Hertzog et al "Recent Advances in the Cannabinoids" Expert Opin in Therapeutics Patents 2004 vol. 14(10) pp. 1435-1452.
Holt et al "Inhibitors of Fatty Acid Amide Hydrolase Reduce Carrageenan-Induced Hind Paw Inflammation in Pentobarbital-Treated Mice: Comparison With Indomethacin and Possible Involvement of Cannabinoid Receptors" Br J of Pharmacology 2005 vol. 146 pp. 467-476.
Howlett et al., "International Union of Pharmacology. XXVII. Classification of Cannabinoid Receptors," Pharmacol Rev. 2002, 54, 161-202.

(56) References Cited

OTHER PUBLICATIONS

Irwin et al "Comprehensive Observational Assessment: 1a. A Systematic Quantitative Procedure for Assessing the Behavioral and Physiolig State of-the Mouse" Phychopharmacologia (BERL) 1968 vol. 13 pp. 222-257.

Jantzen et al "Prodrugs" Modern Pharmaceutics 1996 pp. 596.

Karbarz et al "Biochemical and Biological Properties of 4-(3-Phenyl-[1,2,4] Thiadiazol-5-Yl)-Piperazine-1 Carboxyl Acid Phenylamide, A Mechanism Based Inhibitor of Fatty Acid Amide Hydrolase" Anesth Analog 2009 vol. 108(1) pp. 316-329.

Karsak et al "Cannabinoid Receptor Type 2 Gene Is Associated With Human Osteoporosis" Hum Mol Genet 2005 vol. 14(22) pp. 3389-3396.

Kathuria et al "Modulation of Anxiety Through Blockade of Anandamide Hydrolysis" Nat Med 2003 vol. 9(1) pp. 76-81.

Kirkham et al "Endocannabinoid Levels in Rat Limbic Forebrain and Hypothalamus in Relation to Fasting, Feeding and Satiation: Stimulation of Eating by 2-Arachidonoyl Glycerol" Br J of Pharmcol 2002 vol. 136 pp. 550-557.

Lambert et al., "The Palmitoylethanolamide Family: A New Class of Anti-Inflammatory Agents?" Curr. Med. Chem. 2002, 9(6), 663-674.

Lambert et al., "The Palmitoylethanolamide and Oleamide Enigmas : Are These Two Fatty Acid Amides Cannabimimetic?," Curr Med Chem. 1999, 6, 757-73.

Larsen et al A Textbook of Drug Design and Development Krogsgaard-Larsen et al Harwood Academic Publishers 1991 Index.

McOmie et al Protective Groups in Organic Chemistry 1973 J.F.W. McOmie Plenum Press 1973 Index.

Mendelson et al "The Hypnotic Actions of the Fatty Acid Amide, Oleamide" Neurophychopharmacology 2001 vol. 25(S5) pp. S36-S39.

Metabolite Encyclopedia.com—http://www.encyclopedia.com/doc/1EI-metabolit.html, accessed Jan. 25, 2008.

Ofek et al "Peripheral Cannabinoid Receptor CB2 Regulates Bone Mass" Proc Natl Acad Sci USA 2006 vol. 103 pp. 696-701.

Olah et al., "Anandamide Activates Vanilloid Receptor 1 (VR1) at Acidic PH in Dorsal Root Ganglia Neurons and Cells Ectopically Expressing VR1," J Biol Chem. 2001, 276, 31163-70.

Overton et al "GPR119 A Novel G Protein Coupled Receptor Target for the Treatment of Type 2 Diabetes and Obesity" Br J Pharmacol 2008 vol. 153(1) pp. S76-S81.

Paulekuhn et al "Trends in Active Pharmaceutical Ingredient Salt Selection Based on Analysis of the Orange Book Database" J Med Chem 2007 vol. 50 pp. 6665-6672.

Cravatt_Ahn et al., Biochemistry 2007, 46, 13019-13030.

\* cited by examiner

MODULATORS OF FATTY ACID AMIDE HYDROLASE

CROSS REFERENCE TO RELATED APPLICATIONS

This application is a continuation of U.S. application Ser. No. 13/695,855, filed Nov. 2, 2012, which claims the benefit of International Application No. PCT/US2011/034755 filed May 2, 2011, which claims priority of U.S. provisional patent application Ser. No. 61/330,522, filed on May 3, 2010, the entire disclosures of which are hereby incorporated by reference in their entirety.

FIELD OF THE INVENTION

The present invention relates to the compound 4-(2,2-difluoro-benzo[1,3]dioxol-5-ylmethyl)-piperazine-1-carboxylic acid (4-chloro-pyridin-3-yl)-amide, pharmaceutical compositions containing the compound, methods of synthesizing the compound, and methods of using the compound for the treatment of disease states, disorders, and conditions mediated by fatty acid amide hydrolase (FAAH) activity are provided.

BACKGROUND OF THE INVENTION

Medicinal benefits have been attributed to the cannabis plant for centuries. The primary bioactive constituent of cannabis is $\Delta^9$-tetrahydrocannabinol (THC). The discovery of THC eventually led to the identification of two endogenous cannabinoid receptors responsible for its pharmacological actions, namely $CB_1$ and $CB_2$ (Goya et al., *Exp. Opin. Ther. Patents*, 2000, 10, 1529). These discoveries not only established the site of action of THC, but also inspired inquiries into the endogenous agonists of these receptors, or "endocannabinoids". The first endocannabinoid identified was the fatty acid amide arachidonyl ethanolamide or anandamide (AEA). AEA itself elicits many of the pharmacological effects of exogenous cannabinoids (Piomelli et al., *Nat. Rev. Neurosci.*, 2003, 4(11), 873).

The catabolism of AEA is primarily attributable to the integral membrane bound protein fatty acid amide hydrolase (FAAH), which hydrolyzes AEA to arachidonic acid and ethanolamine. FAAH was characterized in 1996 by Cravatt and co-workers (Cravatt et al., *Nature*, 1996, 384, 83). It was subsequently determined that FAAH is additionally responsible for the catabolism of a large number of important lipid signaling fatty acid amides including: another major endocannabinoid, 2-arachidonoylglycerol (2-AG) (Devane et al., *Science*, 1992, 258, 1946-1949); the sleep-inducing substance, oleamide (Cravatt et al., *Science*, 1995, 268, 1506); the appetite-suppressing agent, N-oleoylethanolamide (OEA) (Rodriguez de Fonseca, *Nature*, 2001, 414, 209); and the anti-inflammatory agent, palmitoylethanolamide (PEA) (Lambert et al., *Curr. Med. Chem.*, 2002, 9(6), 663).

Small-molecule inhibitors of FAAH should elevate the concentrations of these endogenous signaling lipids and thereby produce their associated beneficial pharmacological effects. There have been some reports of the effects of various FAAH inhibitors in pre-clinical models.

In particular, two carbamate-based inhibitors of FAAH were reported to have analgesic properties in animal models. In rats, BMS-1 (see WO 02/087569), which has the structure shown below, was reported to have an analgesic effect in the spinal nerve ligation (Chung) model of neuropathic pain, and the Hargreaves test of acute thermal nociception. URB-597 was reported to have efficacy in the zero plus maze model of anxiety in rats, as well as analgesic efficacy in the rat hot plate and formalin tests (Kathuria et al., *Nat. Med.*, 2003, 9(1), 76). The urea, 4-(3-Phenyl-[1,2,4]thiadiazol-5-yl)-piperazine-1-carboxylic acid phenylamide, was found to be efficacious in both the spinal nerve ligation (Chung) model of neuropathic pain and the mild thermal injury model of acute burn injury pain (Karbarz et al., *Anesth Analg.*, 2009, 108(1), 316-329). Other potent urea inhibitors of the FAAH enzyme have been reported (WO 06/074025). The sulfonylfluoride AM374 was also shown to significantly reduce spasticity in chronic relapsing experimental autoimmune encephalomyelitis (CREAE) mice, an animal model of multiple sclerosis (Baker et al., *FASEB J.*, 2001, 15(2), 300).

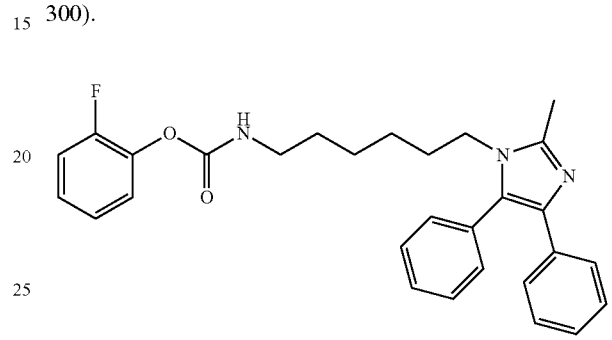

BMS-1

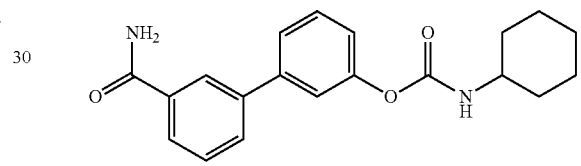

URB-597

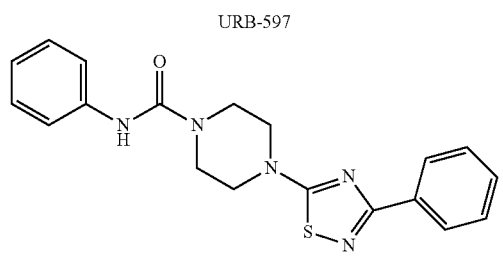

JNJ-1661010

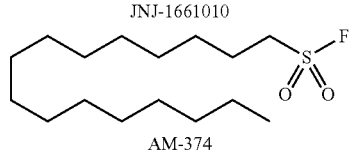

AM-374

In addition, the oxazolopyridine ketone OL-135 is reported to be a potent inhibitor of FAAH with analgesic activity in both the hot plate and tail immersion tests of thermal nociception in rats (WO 04/033652).

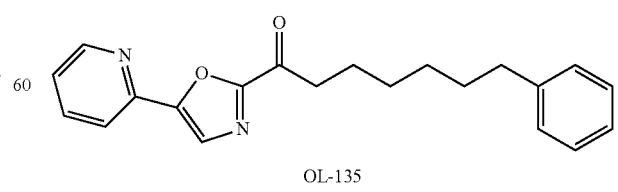

OL-135

Results of research on the effects of certain exogenous cannabinoids has elucidated that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDs who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson et al., Br. J. Psychiatry, 2001, 178, 107-115). Atlantic Pharmaceuticals is reported to be developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain with CT-3 was reportedly initiated in Germany in May 2002.

A number of individuals with locomotor activity-related diseases, such as multiple sclerosis have claimed a benefit from cannabis for both disease-related pain and spasticity, with support from small controlled trials (Croxford et el., J. Neuroimmunol, 2008, 193, 120-9; Svendsen, Br. Med. J., 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by $CB_1$ and $CB_2$ receptors (Baker, Nature, 2000, 404, 84-87). Phase 3 clinical trials have been undertaken in multiple sclerosis and spinal cord injury patients with a narrow ratio mixture of tetrahydrocannabinol/cannabidiol (THC/CBD). It has been reported that FAAH knockout mice consistently recover to a better clinical score than wild type controls, and this improvement is not a result of anti-inflammatory activity, but rather may reflect some neuroprotection or remyelination promoting effect of lack of the enzyme (Webb et al, Neurosci Lett., 2008, vol. 439, 106-110).

Reports of small-scale controlled trials to investigate other potential commercial uses of cannabinoids have been made. Trials in volunteers have been reported to have confirmed that oral, injected, and smoked cannabinoids produced dose-related reductions in intraocular pressure (IOP) and therefore may relieve glaucoma symptoms. Ophthalmologists have prescribed cannabis for patients with glaucoma in whom other drugs have failed to adequately control intraocular pressure (Robson et al., 2001, supra).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH$^{-/-}$ mice show reduced responses in tests of nociception, but did not show catalepsy, hypothermia, or increased feeding behavior (Cravatt et al., Proc. Natl. Acad. Sci. USA, 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham et al., Br. J. Pharmacol., 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli et al., 2003, supra).

In addition to the effects of a FAAH inhibitor on AEA and other endocannabinoids, inhibitors of FAAH's catabolism of other lipid mediators may be used in treating certain other therapeutic indications. For example, PEA has demonstrated biological effects in animal models of inflammation (Holt et al., Br. J. Pharmacol., 2005, 146, 467-476), immunosuppression, analgesia, and neuroprotection (Ueda et al., J. Biol. Chem., 2001, 276(38), 35552). Oleamide, another substrate of FAAH, induces sleep (Boger et al., Proc. Natl. Acad. Sci. USA, 2000, 97(10), 5044; Mendelson et al., Neuropsychopharmacology, 2001, 25, S36). Inhibition of FAAH has also been implicated in cognition (Varvel et al., J. Pharmacol. Exp. Ther., 2006, 317(1), 251-257) and depression (Gobbi et al., Proc. Natl. Acad. Sci. USA, 2005, 102(51), 18620-18625).

Two additional indications for FAAH are supported by recent data indicating that FAAH substrate activated receptors are important in energy metabolism, and in bone homeostasis (Overton et al., Br. J. Pharmacol., 2008, 153 Suppl 1, S76-81; and Plutzky et al., Diab. Vasc. Dis. Res., 2007, 4 Suppl 3, S12-4). It has been shown that one of the previously mentioned lipid signaling fatty acid amides catabolized by FAAH, OEA, is one of the most active agonists of the recently de-orphanised GPCR 119 (GPR119) (also termed glucose-dependent insulinotropic receptor). This receptor is expressed predominantly in the pancreas in humans and activation improves glucose homeostasis via glucose-dependent insulin release in pancreatic beta-cells. GPR119 agonists can suppress glucose excursions when administered during oral glucose tolerance tests, and OEA has also been shown independently to regulate food intake and body weight gain when administered to rodents, indicating a probable benefit in energy metabolism disorders, such as insulin resistance and diabetes. The FAAH substrate PEA is an agonist at the PPARα receptor. Evidence from surrogate markers in human studies with the PPARα agonist fenofibrate is supportive of the concept that PPARα agonism offers the potential for inducing a coordinated PPARα response that may improve dyslipidaemia, repress inflammation and limit atherosclerosis in patients with the metabolic syndrome or type 2 diabetes. Anandamide is an agonist at the PPARγ receptor. Anandamide treatment induces 3T3-L1 differentiation into adipocytes, as well as triglyceride droplet accumulation and expression of adiponectin (Bouaboula et al., E. J. Pharmacol., 2005, 517, 174-181). Low dose cannabinoid therapy has been shown to reduce atherosclerosis in mice, further suggesting a therapeutic benefit of FAAH inhibition in dyslipidemia, liver steatosis, steatohepatitis, obesity, and metabolic syndrome (Steffens et al., Nature, 2005, 434, 782-6).

Osteoporosis is one of the most common degenerative diseases. It is characterized by reduced bone mineral density (BMD) with an increased risk for bone fractures. $CB_2$-deficient mice have a markedly accelerated age-related trabecular bone loss and cortical expansion. A $CB_2$-selective agonist enhances endocortical osteoblast number and activity and restrains trabecular osteoclastogenesis and attenuates ovariectomy-induced bone loss (Ofek et al., Proc. Natl. Acad. Sci. U.S.A., 2006, 103, 696-701). There is a substantial genetic contribution to BMD, although the genetic factors involved in the pathogenesis of human osteoporosis are largely unknown. The applicability to human BMD is suggested by genetic studies in which a significant association of single polymorphisms and haplotypes was found encompassing the CNR2 gene on human chromosome 1p36, demonstrating a role for the peripherally expressed $CB_2$ receptor in the etiology of osteoporosis (Karsak et al., *Hum. Mol. Genet*, 2005, 14, 3389-96).

Thus, small-molecule FAAH inhibitors should be useful in treating pain of various etiologies, anxiety, multiple sclerosis and other movement disorders, nausea/emesis, eating disorders, epilepsy, glaucoma, inflammation, immunosuppression, neuroprotection, depression, cognition enhancement, and sleep disorders, and potentially with fewer side effects than treatment with an exogenous cannabinoid.

A number of heteroaryl-substituted ureas have been reported in various publications. Certain piperazinyl and piperidinyl compounds as FAAH modulators are described in Intl. Patent Appl. No. WO 2006/074025, Intl. Patent Appl. Ser. No. PCT/US2009/065757, Intl. Patent Appl. Ser. No. PCT/US2009/065752, U.S. Appl. Publ. No. US 2009/0062294, and U.S. provisional Appl. Ser. No. 61/263,477. Certain piperazine-1-carboxamide and piperidine-1-carboxamide derivatives are described in Intl. Patent Appl. No. WO 2008/023720. Certain aryloxobutylpiperidines, aryloxobutylpyrrolidines, and aryloxobutylpiperazines are described in Intl. Patent Appl. No. WO 2001/005763. Certain piperidine derivatives are reported in Intl. Patent Appl. No. WO 99/50247. Certain piperazine derivatives are described in Intl. Patent Appl. No. WO 99/42107. Certain N-aralkylpiperazines are described in Intl. Patent Appl. No. WO 98/37077. Certain aryl-substituted heterocyclic urea derivatives are described in U.S. provisional Appl. No. 61/184,606. However, there remains a desire for potent FAAH modulators with suitable pharmaceutical properties.

The features and advantages of the present invention are apparent to one of ordinary skill in the art. Based upon this disclosure, including the summary, detailed description, background, examples, and claims, one of ordinary skill in the art will be able to make modifications and adaptations to various conditions and usages. Publications described herein are incorporated by reference in their entirety.

SUMMARY OF THE INVENTION 4-(2,2-Difluoro-benzo[1,3]dioxol-5-ylmethyl)-piperazine-1-carboxylic acid (4-chloro-pyridin-3-yl)-amide, and pharmaceutically acceptable salts thereof, are herein described, which have been found to have FAAH-modulating activity. The invention is directed to the general and preferred embodiments defined, respectively, and by the independent and dependent claims appended hereto, which are incorporated by reference herein.

The present invention provides experimental evidence demonstrating that the chemical entities of the present invention exhibit higher IC50 values in CYP2D6 inhibition when compared to a comparator compound. Additionally, 4-(2,2-difluoro-benzo[1,3]dioxol-5-ylmethyl)-piperazine-1-carboxylic acid (4-chloro-pyridin-3-yl)-amide exhibited improved behavior and physiological function side effects as a result of compound administration when compared to comparator compound in a primary observation (Irwin) test in rats.

The 4-(2,2-difluoro-benzo[1,3]dioxol-5-ylmethyl)-piperazine-1-carboxylic acid (4-chloro-pyridin-3-yl)-amide $IC_{50}$ activity of CYP2D6 inhibition is improved in comparison to a previously described piperazinyl urea compound, 4-(2,2-difluoro-benzo[1,3]dioxol-5-ylmethylypiperazine-1-carboxylic acid pyridin-3-ylamide (see PCT. Pub. Appl. No. WO 2006/074025, example 150), which is herein described as a comparator compound. 4-(2,2-Difluoro-benzo[1,3]dioxol-5-ylmethyl)-piperazine-1-carboxylic acid (4-chloro-pyridin-3-yl)amide exhibited an $IC_{50}$ value 7.5 to 5.5 times higher versus the comparator compound with bufuralol or dextromethorphan being used as substrates, respectively.

Furthermore, the chemical entities of the present invention display unpredicted characteristics in a primary observation (Irwin) test in rats when compared to the comparator compound. In particular, comparator compound 4-(2,2-difluoro-benzo[1,3]dioxol-5-ylmethyl)-piperazine-1-carboxylic acid pyridin-3-ylamide increased reactivity to touch in all rats tested at the 10 mg/kg dose while 4-(2,2-difluoro-benzo[1,3]dioxol-5-ylmethyl)-piperazine-1-carboxylic acid (4-chloro-pyridin-3-yl)-amide induced reactivity in only one of four rats tested at the same dosage. The comparator compound induced sedation at the 15 to 120 minute interval and abnormal gait (rolling) at 15 minutes post treatment in all rats tested at 60 mg/kg while such observations were not apparent in 4-(2,2-difluoro-benzo[1,3]dioxol-5-ylmethyl)-piperazine-1-carboxylic acid (4-chloro-pyridin-3-yl)-amide treated rats. Also apparent at the 60 mg/kg dosage, the comparator compound decreased muscle tone for all rats in the 60 to 120 minute time interval while 4-(2,2-difluoro-benzo[1,3]dioxol-5-ylmethyl)-piperazine-1-carboxylic acid (4-chloro-pyridin-3-yl)-amide increased abdominal muscle tome in only one of four rats tested. Finally, at 60 mg/kg dosing the comparator compound induced hypothermia in rat subjects at 15 to 60 minute and 180 minute intervals while this observation was absent in rats tested with the compound of the present invention.

In one general aspect, the invention is directed to the compound of 4-(2,2-difluoro-benzo[1,3]dioxol-5-ylmethyl)-piperazine-1-carboxylic acid (4-chloro-pyridin-3-yl)-amide. In a particular embodiment, the compound is a hydrochloride salt of 4-(2,2-difluoro-benzo[1,3]dioxol-5-ylmethyl)-piperazine-1-carboxylic acid (4-chloro-pyridin-3-yl)-amide.

The invention also relates to pharmaceutically acceptable salts of 4-(2,2-difluoro-benzo[1,3]dioxol-5-ylmethylypiperazine-1-carboxylic acid (4-chloro-pyridin-3-yl)-amide, pharmaceutically acceptable prodrugs of 4-(2,2-difluoro-benzo[1,3]dioxol-5-ylmethyl)-piperazine-1-carboxylic acid (4-chloro-pyridin-3-yl)-amide, and pharmaceutically acceptable metabolites of 4-(2,2-difluoro-benzo[1,3]dioxol-5-ylmethyl)-piperazine-1-carboxylic acid (4-chloro-pyridin-3-yl)-amide.

In a further general aspect, the invention relates to pharmaceutical compositions each comprising: (a) a therapeutically effective amount of at least one of 4-(2,2-difluoro-benzo[1,3]dioxol-5-ylmethyl)-piperazine-1-carboxylic acid (4-chloro-pyridin-3-yl)-amide, pharmaceutically acceptable salts of 4-(2,2-difluoro-benzo[1,3]dioxol-5-ylmethyl)-piperazine-1-carboxylic acid (4-chloro-pyridin-3-yl)-amide, pharmaceutically acceptable prodrugs of 4-(2,2-difluoro-benzo[1,3]dioxol-5-ylmethyl)-piperazine-1-carboxylic acid (4-chloro-pyridin-3-yl)-amide, and pharmaceutically acceptable metabolites of 4-(2,2-difluoro-benzo[1,3]dioxol-5-ylmethyl)-piperazine-1-carboxylic acid (4-chloro-pyridin-3-yl)-amide; and (b) a pharmaceutically acceptable excipient.

In another aspect, embodiments of the invention are useful as FAAH modulators. Thus, the invention is directed to a method for modulating FAAH activity, comprising exposing FAAH to a therapeutically effective amount of at least one of 4-(2,2-difluoro-benzo[1,3]dioxol-5-ylmethyl)- piperazine-1-carboxylic acid (4-chloro-pyridin-3-yl)-amide, pharmaceutically acceptable salts of 4-(2,2-difluoro-benzo [1,3]dioxol-5-ylmethylypiperazine-1-carboxylic acid (4-chloro-pyridin-3-yl)-amide, pharmaceutically acceptable prodrugs of 4-(2,2-difluoro-benzo[1,3]dioxol-5-ylmethyl)-piperazine-1-carboxylic acid (4-chloro-pyridin-3-yl)-amide, and pharmaceutically active metabolites of 4-(2,2-difluoro-benzo[1,3]dioxol-5-ylmethyl)-piperazine-1-carboxylic acid (4-chloro-pyridin-3-yl)-amide.

In another general aspect, the invention is directed to a method of treating a subject suffering from or diagnosed with a disease, disorder, or medical condition mediated by fatty acid amide hydrolase (FAAH) activity, comprising administering to the subject in need of such treatment an effective amount of at least one agent selected from 4-(2,2-difluoro-benzo[1,3]dioxol-5-ylmethyl)-piperazine-1-carboxylic acid (4-chloro-pyridin-3-yl)-amide and its pharmaceutically acceptable salts, pharmaceutically active prodrugs, and pharmaceutically active metabolites. In preferred embodiments of the inventive method, the disease, disorder, or medical condition is selected from: anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, Niemann-Pick disease, Parkinson's disease, Huntington's chorea, optic neuritis, autoimmune uveitis, symptoms of drug or alcohol withdrawal, nausea, emesis, sexual dysfunction, anxiety, post-traumatic stress disorder, cerebral vasospasm, glaucoma, irritable bowel syndrome, inflammatory bowel disease, immunosuppression, itch, gastroesophageal reflux disease, paralytic ileus, secretory diarrhea, gastric ulcer, rheumatoid arthritis, unwanted pregnancy, hypertension, cancer, hepatitis, allergic airway disease, auto-immune diabetes, intractable pruritis, neuroinflammation, diabetes, metabolic syndrome, osteoporosis, dyslipidemia, liver steatosis, and steatohepatitis.

In another general aspect, the invention is directed towards a method of synthesizing 4-(2,2-difluoro-benzo[1,3]dioxol-5-ylmethyl)-piperazine-1-carboxylic acid (4-chloro-pyridin-3-yl)-amide using 2,2-difluoro-benzo[1,3]dioxole-5-carbaldehyde and piperazine in a single step hydrogenation reaction.

Additional embodiments, features, and advantages of the invention will be apparent from the following detailed description and through practice of the invention.

DETAILED DESCRIPTION OF THE INVENTION AND ITS PREFERRED EMBODIMENTS

The invention may be more fully appreciated by reference to the following description, including the following glossary of terms and the concluding examples. For the sake of brevity, the disclosures of the publications cited in this specification are herein incorporated by reference.

As used herein, the terms "including", "containing" and "comprising" are used herein in their open, non-limiting sense.

A structural formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, or fluorine, such as $^2$H, $^3$H, $^{11}$C, $^{13}$C, $^{14}$C, $^{15}$N, $^{18}$O, $^{17}$O, and $^{18}$F, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT), including drug or substrate tissue distribution assays, or in radioactive treatment of patients. In particular, an $^{18}$F- or $^{11}$C-labeled compound may be preferred for PET or SPECT studies. Further, substitution with heavier isotopes such as deuterium (i.e., $^2$H) may afford certain therapeutic advantages resulting from greater metabolic stability, for example, increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

In one general embodiment, the invention relates to 4-(2,2-difluoro-benzo[1,3]dioxol-5-ylmethyl)-piperazine-1-carboxylic acid (4-chloro-pyridin-3-yl)-amide and pharmaceutically acceptable salts, pharmaceutically acceptable prodrugs, and pharmaceutically active metabolites of such a compound. In another general embodiment, the invention relates to pharmaceutical compositions each comprising a therapeutically effective amount of a FAAH-modulating agent selected from 4-(2,2-difluoro-benzo[1,3]dioxol-5-ylmethyl)-piperazine-1-carboxylic acid (4-chloro-pyridin-3-yl)-amide and pharmaceutically acceptable salts, pharmaceutically acceptable prodrugs, and pharmaceutically active metabolites of such a compound.

The invention also relates to pharmaceutically acceptable salts of 4-(2,2-difluoro-benzo[1,3]dioxol-5-ylmethyl)-piperazine-1-carboxylic acid (4-chloro-pyridin-3-yl)-amide. A "pharmaceutically acceptable salt" is intended to mean a salt of a free acid or base of a compound of 4-(2,2-difluoro-benzo[1,3]dioxol-5-ylmethyl)-piperazine-1-carboxylic acid (4-chloro-pyridin-3-yl)-amide that is non-toxic, biologically tolerable, or otherwise biologically suitable for administration to the subject. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

In certain embodiments, the compound, 4-(2,2-difluoro-benzo[1,3]dioxol-5-ylmethyl)-piperazine-1-carboxylic acid (4-chloro-pyridin-3-yl)-amide, is a hydrochloride salt.

A compound of 4-(2,2-difluoro-benzo[1,3]dioxol-5-ylmethyl)-piperazine-1-carboxylic acid (4-chloro-pyridin-3-yl)amide may possess a sufficiently basic group and accordingly may react with a number of inorganic and organic acids, to form a pharmaceutically acceptable salt.

The compound of the invention contains at least one basic nitrogen, therefore, a desired pharmaceutically acceptable salt may be prepared by any suitable method available in the art, for example, by treatment of the free base with an inorganic acid, such as hydrochloric acid, hydrobromic acid, sulfuric acid, sulfamic acid, nitric acid, boric acid, phosphoric acid, and the like; or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid; an amino acid, such as aspartic acid or glutamic acid; an aromatic acid, such as benzoic acid, 2-acetoxybenzoic acid, naphthoic acid, or cinnamic acid; a sulfonic acid, such as laurylsulfonic acid, p-toluenesulfonic acid, methanesulfonic acid, or ethanesulfonic acid; or any other acid and mixture thereof that are regarded as equivalents or acceptable substituents in light of the ordinary level of skill in this art.

The invention also relates to pharmaceutically acceptable prodrugs of 4-(2,2-difluoro-benzo[1,3]dioxol-5-ylmethyl)-piperazine-1-carboxylic acid (4-chloro-pyridin-3-yl)-amide. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Example 1). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino group of 4-(2,2-difluoro-benzo[1,3]dioxol-5-ylmethyl)-piperazine-1-carboxylic acid (4-chloro-pyridin-3-yl)-amide. Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs may be produced, for instance, by derivatizing free amines as amides, sulfonamides or phosphonamides.

The present invention also relates to pharmaceutically active metabolites of 4-(2,2-difluoro-benzo[1,3]dioxol-5-ylmethyl)-piperazine-1-carboxylic acid (4-chloro-pyridin-3-yl)-amide. A "pharmaceutically active metabolite" means a pharmacologically active product of metabolism in the body of 4-(2,2-difluoro-benzo[1,3]dioxol-5-ylmethyl)-piperazine-1-carboxylic acid (4-chloro-pyridin-3-yl)-amide or a salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

A compound of 4-(2,2-difluoro-benzo[1,3]dioxol-5-ylmethyl)-piperazine-1-carboxylic acid (4-chloro-pyridin-3-yl)-amide, and its pharmaceutically acceptable salts, pharmaceutically acceptable prodrugs, and pharmaceutically active metabolites (collectively, "active agents") of the present invention are useful as FAAH inhibitors in the methods of the invention. The term "inhibitors" refers to compounds that decrease, prevent, inactivate, desensitize or down-regulate FAAH expression or activity. The active agents may be used in the inventive methods for the treatment of medical conditions, diseases, or disorders mediated through inhibition or modulation of FAAH, such as those described herein. Active agents according to the invention may therefore be used as an analgesic, anti-depressant, cognition enhancer, neuroprotectant, sedative, appetite stimulant/suppressor, or contraceptive.

Exemplary medical conditions, diseases, and disorders mediated by FAAH activity include anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, epilepsy, Niemann-Pick disease, Parkinson's disease, Huntington's chorea, optic neuritis, autoimmune uveitis, symptoms of drug or alcohol withdrawal, nausea, emesis, sexual dysfunction, post-traumatic stress disorder, cerebral vasospasm, diabetes, metabolic syndrome, osteoarthritis and osteoporosis.

Thus, the active agents may be used to treat subjects diagnosed with or suffering from such a disease, disorder, or condition. The term "treat" or "treating" as used herein is intended to refer to administration of an agent or composition of the invention to a subject for the purpose of effecting a therapeutic benefit through inhibition of FAAH activity. Treating includes reversing, ameliorating, alleviating, inhibiting the progress of, lessening the severity of, reducing the incidence of, or preventing a disease, disorder, or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize, or up-regulate FAAH expression or activity.

Accordingly, the invention relates to methods of using the active agents described herein to treat subjects diagnosed with or suffering from a disease, disorder, or condition mediated through FAAH activity, such as: anxiety, pain, sleep disorders, eating disorders, inflammation, movement disorders (e.g., multiple sclerosis), glucose and lipid metabolism (e.g. diabetes) and bone homeostasis (e.g. osteoporosis).

Symptoms or disease states are intended to be included within the scope of "medical conditions, disorders, or diseases." For example, pain may be associated with various diseases, disorders, or conditions, and may include various etiologies. Illustrative types of pain treatable with a FAAH-modulating agent, in one example herein a FAAH-inhibiting agent, according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In treatment methods according to the invention, an effective amount of at least one active agent according to the invention is administered to a subject suffering from or diagnosed as having such a disease, disorder, or condition. A "therapeutically effective amount" or "effective amount" means an amount or dose of a FAAH-modulating agent sufficient to generally bring about a desired therapeutic benefit in patients in need of treatment for a disease, disorder, or condition mediated by FAAH activity. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.0001 to about 200 mg of active agent per kg of subject's body weight per day, preferably about 0.001 to 100 mg/kg/day, or about 0.01 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 5 g/day. Once improvement of the patient's disease, disorder, or condition has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be co-administered separately with an active agent of 4-(2,2-difluoro-benzo[1,3]dioxol-5-ylmethyl)-piperazine-1-carboxylic acid (4-chloro-pyridin-3-yl)-amide, or included with such an agent in a pharmaceutical composition according to the invention. In an exemplary embodiment, additional active ingredients are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention. In one illustrative embodiment, a composition according to the invention may contain one or more additional active ingredients selected from opioids, non-steroidal anti-inflammatory drugs (NSAID) (e.g., ibuprofen, cyclooxygenase-2 (COX-2) inhibitors, and naproxen), gabapentin, pregabalin, tramadol, acetaminophen, and aspirin.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Certain pharmaceutically acceptable excipients are reviewed in "Handbook of Pharmaceutical Excipients", $6^{th}$ ed., Pharmaceutical Press, 2009. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 5 mg to 5 g daily, or from about 50 mg to 5 g daily, in single or divided doses. For example, a total daily dosage of about 5 mg to 5 g daily may be accomplished by dosing once, twice, three, or four times per day.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary active agents useful in methods of the invention will now be described by reference to illustrative synthetic schemes for their general preparation below and the specific examples that follow.

The compounds as described above may be made according to processes within the skill of the art and/or that are described in the schemes and examples that follow. Certain reaction schemes may occur with or without protection as appropriate. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", 3$^{rd}$ ed., John Wiley & Sons, 1999. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention.

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

The synthesis of 4-(2,2-difluoro-benzo[1,3]dioxol-5-ylmethyl)-piperazine-1-carboxylic acid (4-chloro-pyridin-3-yl)-amide will now be described by reference to illustrative synthetic schemes and a specific protocol for its preparation. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent.

SCHEME A

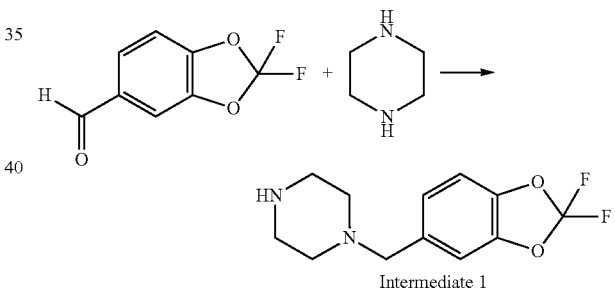

Intermediate 1

Referring to Scheme A, Intermediate 1 was obtained by reacting 2,2-difluoro-benzo[1,3]dioxole-5-carbaldehyde with piperazine under hydrogenation conditions. The reaction can be carried out using Pd(OH)$_2$, Pt, or Pd as a catalyst, in solvents such as MeOH, EtOH, or AcOH. The reaction can be performed at temperatures between 20 to 80° C. Acceptable H$_2$ pressure may be between 1 to 60 bars. The amount of 2,2-difluoro-benzo[1,3]dioxole-5-carbaldehyde to piperazine is typically one to six equivalents. The reaction can be performed on a batch-hydrogenation apparatus or a flow-hydrogenation apparatus.

SCHEME B

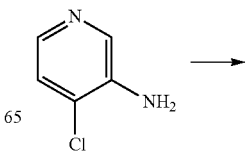

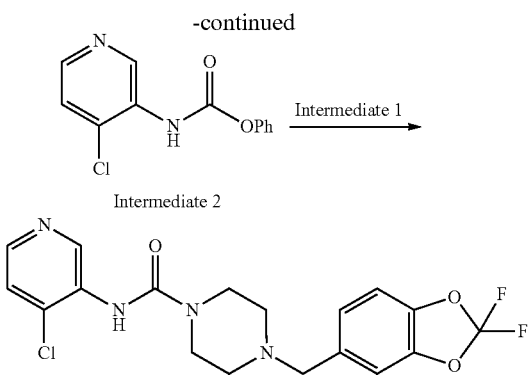

Referring to Scheme B, 4-(2,2-difluoro-benzo[1,3]dioxol-5-ylmethyl)-piperazine-1-carboxylic acid (4-chloro-pyridin-3-yl)-amide was prepared from 3-amino-4-chloropyridine and Intermediate 1. 3-Amino-4-chloropyridine was treated with phenyl chloroformate and pyridine in a solvent such as toluene to give the compound of Intermediate 2. Intermediate 2 was directly reacted with Intermediate 1 to give 4-(2,2-difluoro-benzo[1,3]dioxol-5-ylmethyl)-piperazine-1-carboxylic acid (4-chloro-pyridin-3-yl)-amide.

Chemistry:

In preparing 4-(2,2-difluoro-benzo[1,3]dioxol-5-ylmethyl)-piperazine-1-carboxylic acid (4-chloro-pyridin-3-yl)-amide and the comparator example below, the following general experimental and analytical methods were used.

Reaction mixtures were stirred under a nitrogen atmosphere unless otherwise noted. Where solutions or mixtures are concentrated, they are typically concentrated under reduced pressure using a rotary evaporator.

Mass spectra were obtained on an Agilent series 1100 MSD using electrospray ionization (ESI) in positive mode unless otherwise indicated.

NMR spectra were obtained using either a Bruker model DPX400 (400 MHz), DPX500 (500 MHz), DRX600 (600 MHz) spectrometer. The format of the $^1$H NMR data below is: chemical shift in ppm down field of the tetramethylsilane reference (multiplicity, coupling constant J in Hz, integration).

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Intermediate 1

1-(2,2-Difluoro-benzo[1,3]dioxol-5-ylmethyl)-piperazine

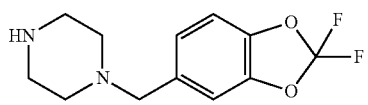 [SMILES: FC1(F)Oc2ccc(CN3CCNCC3)cc2O1]

A 2 L Erlenmeyer flask was charged with piperazine (185.1 g, 2.15 mol), 2,2-difluoro-benzo[1,3]dioxole-5-carbaldehyde (100.0 g, 0.537 mol), and methanol (1.08 L). The solution was stirred at room temperature for 18 h then passed twice through an H-Cube Midi™ (ThalesNano, Budapest, Hungary) with a new 20% Pd(OH)$_2$/C MidiCart cartridge, at the following settings: 70° C., 1 atm pressure, 6 mL/min flow rate, and 10% excess H$_2$ production. The aldehyde starting material was >90% consumed after the first pass, and completely consumed after the second pass as indicated by HPLC analysis. The methanol was evaporated, toluene (1.20 L) was added and the mixture was stirred at room temperature for 18 h. The resulting white suspension was filtered and the solid was rinsed with toluene (200 mL). The combined filtrate was washed with water (2×300 mL), dried over Na$_2$SO$_4$, filtered, and concentrated to afford the product as a colorless oil. The oil was dissolved in heptane (100 mL) and the product was allowed to crystallize at room temperature. For subsequent synthesis experiments, addition of a small amount of seed crystals was used to quicken the crystallization process. The suspension was cooled to 0° C., filtered and the solid was dried in vacuum oven at 50° C. for 24 h to give the title compound as a white solid (108.0 g, 78%). The heptane filtrate was concentrated to approximately 20 mL followed by addition of product seed crystals. The solution then was stirred overnight. The second batch of the title compound was obtained as a white solid after filtration and drying (6.7 g, 5%). The combined yield was (115 g, 83%). MS (ESI$^+$): calcd for C$_{12}$H$_{14}$F$_2$N$_2$O$_2$ m/z 256.1. found 256.9 (M+H)$^+$. $^1$H NMR (400 MHz, CDCl$_3$) δ: 7.11 (d, J=0.9 Hz, 1H), 6.99 (dd, J=9.0, 0.9 Hz, 1H), 6.95 (d, J=9.0 Hz, 1H), 3.45 (s, 2H), 2.92-2.83 (m, 4H), 2.39 (s, 4H); $^{13}$C NMR (101 MHz, CDCl$_3$) δ: 143.89, 142.72, 134.68, 131.65 (t, JC-F=255.3), 123.88, 110.13, 108.82, 63.10, 54.38, 46.07.

Example 1

4-(2,2-difluoro-benzo[1,3]dioxol-5-ylmethyl)-piperazine-1-carboxylic acid (4-chloro-pyridin-3-yl)-amide

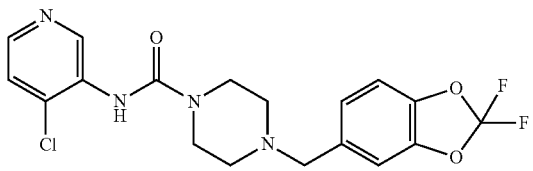 [SMILES: O=C(Nc1cnccc1Cl)N1CCN(Cc2ccc3c(c2)OC(F)(F)O3)CC1]

A 2 L, three-neck Morton flask equipped with a mechanical stirrer, thermocouple, and addition funnel under a nitrogen atmosphere was charged with 3-amino-4-chloropyridine (35.0 g, 272 mmol) and toluene (740 mL). The brown solution was cooled to 2° C. Pyridine (25.3 mL, 310 mmol) was added in one portion, followed by the dropwise addition of phenyl chloroformate (32.6 mL, 259 mmol) over 30 min. The maximum internal temperature was 5° C. After stirring at 2-5° C. for 7 h the reaction mixture became a thick yellow suspension. A cooled solution of K$_2$CO$_3$ (53.6 g, 388 mmol) in water (216 mL) was added over 3 min, during which the maximum internal temperature was 6° C. 1-(2,2-Difluoro-benzo[1,3]dioxol-5-ylmethyl)-piperazine (66.3 g, 259 mmol) was then added as a solid over 1 min. The mixture was allowed to warm slowly to room temperature and stirred for 15 h. Water (200 mL) was added and the toluene layer was separated and extracted with aqueous HCl (1.8 M, 600 mL). The aqueous extract was washed with toluene (2×300 mL). MeOH (500 mL) was added to the aqueous layer and the solution was cooled to 5° C. The pH was adjusted to pH 8-9 with the addition of NaOH solution (50 wt %, ca. 50 mL). The addition was at such a rate that the internal temperature did not exceed 17° C. The resulting suspension was stirred at 5° C. for 2 h. The product was collected by filtration and rinsed with MeOH/H$_2$O (1:1, 70 mL). The solid was dried in vacuum oven at 50° C. for 24 h to afford the title compound as a yellow/green solid (73 g, 69%).

A 1 L, three-neck Morton flask equipped with a stir bar, thermocouple, and reflux condenser was charged with crude 4-(2,2-difluoro-benzo[1,3]dioxol-5-ylmethyl)-piperazine-1-carboxylic acid (4-chloro-pyridin-3-yl)-amide (98 g, 239 mmol) and isopropyl acetate (318 mL). The suspension was heated to 65° C., treated with activated charcoal (10.0 g) and stirred at 65° C. for 1 h. The mixture was then heated to 80° C. and quickly filtered through a thin celite pad. The filtrate was slowly cooled to room temperature and then placed in an ice bath for 30 min. The solid was collected by filtration, rinsed with cold iPrOAc (10 mL), and dried to give product 4-(2,2-difluoro-benzo[1,3]dioxol-5-ylmethyl)-piperazine-1-carboxylic acid (4-chloro-pyridin-3-yl)-amide as a yellow solid (72 g, 73%).

A 2 L, three-neck Morton flask equipped with a mechanical stirrer, thermocouple, and reflux condenser was charged with crude product 4-(2,2-difluoro-benzo[1,3]dioxol-5-ylmethylpiperazine-1-carboxylic acid (4-chloro-pyridin-3-yl)-amide (191 g, 465 mmol) and isopropyl acetate (705 mL). The suspension was heated to 65° C., treated with activated charcoal (11.2 g) and stirred at 65° C. for 1 h. The mixture was then heated to 75° C. and quickly filtered. The filtrate was slowly cooled to room temperature overnight and then placed in an ice bath for 30 min. The solid was collected by filtration, rinsed with cold iPrOAc (40 mL), and dried in vacuum oven at 50° C. for 72 h. The product 4-(2,2-difluoro-benzo[1,3]dioxol-5-ylmethyl)-piperazine-1-carboxylic acid (4-chloro-pyridin-3-yl)-amide was obtained as a slightly yellow solid (161 g, 84%). MS (ESI$^+$): calcd for C$_{18}$H$_{17}$ClF$_2$N$_4$O$_3$ m/z 410.1. found 411.1 (M+H)$^+$. Anal. Calcd for C$_{18}$H$_{17}$ClF$_2$N$_4$O$_3$: C, 52.63; H, 4.17; N, 13.64. Found: C, 52.73; H, 4.15; N, 13.62; $^1$H NMR (600 MHz, CDCl$_3$) δ: 9.36 (s, 1H), 8.19 (d, J=5.2 Hz, 1H), 7.29 (dd, J=5.3, 0.3 Hz, 1H), 7.13 (d, J=0.9 Hz, 1H), 7.02-6.98 (m, 2H), 6.84 (s, 1H), 3.58-3.54 (m, 4H), 3.53 (s, 2H), 2.54-2.48 (m, 4H); $^{13}$C NMR (151 MHz, CDCl$_3$) δ: 153.49, 144.02, 143.88, 143.28, 142.98, 134.05, 133.09, 131.66 (t, JC-F=254.6 Hz), 131.55, 123.89, 123.53, 110.03, 109.02, 62.28, 52.47, 44.23.

Example 1a 4-(2,2-difluoro-benzo[1,3]dioxol-5-ylmethyl)-piperazine-1-carboxylic acid (4-chloro-pyridin-3-yl)-amide, bis hydrochloride

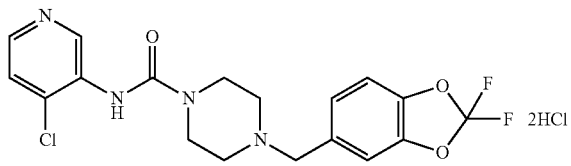 [SMILES: O=C(Nc1cnccc1Cl)N1CCN(Cc2ccc3c(c2)OC(F)(F)O3)CC1]

A solution consisting of 4-(2,2-difluoro-benzo[1,3]dioxol-5-ylmethyl)-piperazine-1-carboxylic acid (4-chloro-pyridin-3-yl)-amide (5.0 g, 12 mmol) and ethanol (200 mL) was treated with saturated aqueous HCl (3.0 mL, 3 equiv). The solvent was removed in vacuo, ethanol (100 mL) was added and the suspension was cooled to 0° C. and filtered.

The resulting white solid was rinsed with cold ethanol (25 mL) and dried under vacuum to give 4-(2,2-difluoro-benzo[1,3]dioxol-5-ylmethyl)-piperazine-1-carboxylic acid (4-chloro-pyridin-3-yl)-amide bis-hydrochloride (4.25 g, 72%). $^1$H NMR (400 MHz, DMSO) δ 11.61 (br s, 1H), 8.98 (s, 1H), 8.65 (s, 1H), 8.37 (d, J=5.4 Hz, 1H), 7.78 (d, J=1.4 Hz, 1H), 7.69 (d, J=5.4 Hz, 1H), 7.52 (d, J=8.3 Hz, 1H), 7.46 (dd, J=8.3, 1.5 Hz, 1H), 4.39 (s, 2H), 4.28-4.12 (m, 2H), 3.49-3.26 (m, 4H), 3.03 (s, 2H).

Comparator Compound: 4-(2,2-Difluoro-benzo[1,3]dioxol-5-ylmethyl)-piperazine-1-carboxylic acid pyridin-3-ylamide

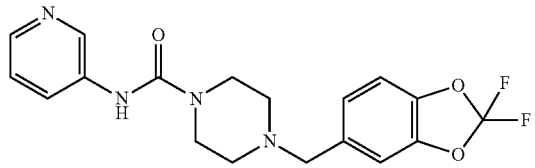 [SMILES: O=C(Nc1cccnc1)N1CCN(Cc2ccc3c(c2)OC(F)(F)O3)CC1]

Pyridin-3-yl-carbamic acid phenyl ester: To a solution consisting of pyridin-3-yl amine (9.49 g, 101 mmol) and pyridine (8.77 g, 111 mmol) in CH$_3$CN (80 mL) at 0° C. was added phenyl chloroformate (15.8 g, 101 mmol) dropwise. The reaction mixture was allowed to warm to room temperature and stirred for 2 h. The reaction was quenched with H$_2$O (200 mL) and the resulting precipitate was filtered and dried under vacuum to provide the title compound as a tan solid (17.34 g, 80%). MS (ESI$^+$): calcd for C$_{12}$H$_{10}$N$_2$O$_2$ m/z 214.07. found 215.3 (M+H)$^+$. $^1$H NMR (500 MHz, d$^6$-DMSO): 10.46 (s, 1H), 8.69 (d, J=2.4 Hz, 1H), 8.27 (dd, J=4.7, 1.4 Hz, 1H), 7.93 (d, J=8.4 Hz, 1H), 7.47-7.41 (m, 2H), 7.37 (dd, J=8.4, 4.7 Hz, 1H), 7.31-7.22 (m, 3H).

4-(2,2-difluoro-benzo[1,3]dioxol-5-ylmethyl)-piperazine-1-carboxylic acid pyridin-3-ylamide: To a solution of pyridine-3-yl-carbamic acid phenyl ester (9.08 g, 42.4 mmol) in DMSO (84 mL) was added 1-(2,2-difluoro-benzo[1,3]dioxol-5-ylmethyl)-piperazine (11.4 g, 44.5 mmol). The reaction mixture was stirred at room temperature for 16 h, then treated with water (130 mL). The resulting solid was isolated by filtration, rinsed with water (4×50 mL) and dried under vacuum. The solid was recrystallized (EtOH—H$_2$O) to give 4-(2,2-difluoro-benzo[1,3]dioxol-5-ylmethyl)-piperazine-1-carboxylic acid pyridin-3-ylamide (13.4 g, 84%). MS (ESI$^+$): calcd for C$_{18}$H$_{18}$F$_2$N$_4$O$_3$ m/z 376.13. found 377.1 (M+H)$^+$. $^1$H NMR (CDCl$_3$): 8.46 (d, J=2.5 Hz, 1H), 8.23-8.21 (m, 1H), 7.99-7.96 (m, 1H), 7.22-7.19 (m, 2H), 7.11 (s, 1H), 6.99-6.98 (m, 2H), 3.54-3.52 (m, 4H), 3.49 (s, 2H, 2.46-2.44 (m, 4H).

Biological Testing:

Assay Method 1

A. Transfection of Cells with Human FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% CO$_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 µL complete media and transferred to an electroporation cuvette with a 0.4 cm gap between the electrodes. Supercoiled human FAAH cDNA (1 μg) was added to the cells and mixed. The voltage for the electroporation was set at 0.25 kV, and the capacitance was set at 960 μF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 μg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 μL of the cell homogenate, 10 μL of the test compound, and 40 μL of anandamide [1-$^3$H-ethanolamine] ($^3$H-AEA, Perkin-Elmer, 10.3 C$_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 μL of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount.

Assay Method 2

A. Transfection of Cells with Rat FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% CO$_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 μL complete media and transferred to an electroporation cuvette with a 0.4 cm gap between the electrodes. Supercoiled rat FAAH cDNA (1 μg) was added to the cells and mixed. The voltage for the electroporation was set at 0.25 kV, and the capacitance was set at 960 μF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 μg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

Transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 μL of the cell homogenate, 10 μL of the test compound, and 40 μL of anandamide [1-$^3$H-ethanolamine] ($^3$H-AEA, Perkin-Elmer, 10.3 C$_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 μg of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount.

Results for compounds tested in these assays are summarized in Table 1, as an average of results obtained. Compounds were tested in either their free base or hydrochloride salt form. The comparator compound, 4-(2,2-difluoro-benzo[1,3]dioxol-5-ylmethylpiperazine-1-carboxylic acid pyridin-3-ylamide, was synthesized as described in PCT. Pub. Appl. No. WO 2006/074025, example 150.

TABLE 1

| Compound | Assay 1<br>IC$_{50}$ (nM) | Assay 2<br>IC$_{50}$ (nM) |
| --- | --- | --- |
| Example 1 | 75 | 320 |
| Comparator Compound | 340 | 450 |

Drug-Drug Interaction (DDI) Assay

The potential for 4-(2,2-difluoro-benzo[1,3]dioxol-5-yl-methyl)-piperazine-1-carboxylic acid (4-chloro-pyridin-3-yl)-amide and Comparator Compound, 4-(2,2-difluoro-benzo[1,3]dioxol-5-ylmethyl)-piperazine-1-carboxylic acid pyridin-3-ylamide, to inhibit human cytochrome P-450 isoenzymes (CYPs) was investigated by incubating the compound at various concentrations with human liver microsomes and specific CYP probe substrates (Table 2). CYP inhibition can impact the safety profile of a drug substance by interfering with the metabolism of other drug molecules.

The assay was set up and executed using a Biomek FXp robotic liquid handling workstation (Beckman Coulter Corp., Fullerton, Calif.), integrated with a Cytomat shaking incubator set at 37° C. (Thermo Electron Corp., Bellefonte, Pa.). A batch of human liver microsomes from 50 donors, pooled and characterized by BD Gentest, (Cat #457111, lot 01220, 20 mg/mL in 250 mM sucrose) was used. Each substrate was incubated at a protein concentration of 0.1, 0.15 or 0.2 mg/mL in a total incubation volume of 0.16 mL. The incubates were prepared in 100 mM potassium phosphate buffer (pH 7.4) supplemented with 5 mM magnesium chloride and 1 mM EDTA. Quinidine was used as a positive control inhibitor for CYP2D6. Quinidine was prepared as a working solution in organic solvent (primarily methanol, with DMSO and acetonitrile as secondary solvents) and was spiked into the microsomal suspension to yield the desired concentration level. The solution was then serially diluted with additional microsomal suspension to yield eight concentration levels. Final organic content was less than 0.07%. A stock solution of the test compound was prepared at a concentration of 50 mM or higher, if possible, in an adequate organic solvent (DMSO, methanol or acetonitrile), depending on solubility limitations. The stock solution was serially diluted with methanol and subsequently spiked into the microsomal suspension to yield final incubation concentrations of 0, 0.1, 0.3, 1, 3, 10, 30 and 100 µM for Comparator Compound and 0, 0.06, 0.18, 0.6, 1.8, 6, 18 and 60 µM for 4-(2,2-difluoro-benzo[1,3]dioxol-5-ylmethyl)-piperazine-1-carboxylic acid (4-chloro-pyridin-3-yl)-amide. The final organic content was 0.2%. Incubations were performed in triplicate for each probe substrate.

The control inhibitor (quinidine) and marker substrate (dextromethorphan or bufuralol) were transferred to the incubation vessels (60 µL aliquots each). After a pre-incubation period at 37° C., the reactions were initiated by the addition of a 40 µL aliquot of NADPH regenerating system (BD Gentest). A 40 µL aliquot (diluted 6:19 with incubation buffer) provided final concentrations of 1.3 mM NADP+, 3.3 mM glucose-6-phosphate and 0.4 U/mL glucose-6-phosphate dehydrogenase. Incubation times were 12 minutes for both dextromethorphan and bufuralol. Reactions were terminated by the direct addition of acetonitrile (160 µL) to the incubation mix followed by transfer to a pooling plate containing additional acetonitrile (400 µL).

The incubation reactions were pooled by equal test compound or control inhibitor concentration, transferred to a Phenomenex Strata™ Impact protein precipitation filter plate containing acetonitrile and internal standards (100 µL of a mixture of the following deuterated compounds ranging in concentration from 0.5 to 2.8 µM: hydroxybufuralol-$d_9$, dextrorphan-$d_3$). The resulting filtrate was evaporated to dryness under a nitrogen flow, then reconstituted in 250 µL mobile phase (1:1 methanol:water, containing 0.1% acetic acid). Samples and standards were analyzed on a Sciex API4000 triple quadrupole mass spectrometer. The data were acquired in Analyst 1.4.1 (Applied Biosystems/MDS Sciex). For $IC_{50}$ assays, the area ratios of the metabolite and internal standard chromatographic peaks were transferred to SigmaPlot (version 8.0) and plotted on a semi-log scale (percent residual activity vs. inhibitor concentration) to determine the $IC_{50}$ value.

4-(2,2-difluoro-benzo[1,3]dioxol-5-ylmethyl)-piperazine-1-carboxylic acid (4-chloro-pyridin-3-yl)-amide inhibited CYP2D6 with an $IC_{50}$ value of 24 µM using Bufuralol as the test substrate, and 11 µM using Dextromorphan as the test substrate. 4-(2,2-difluoro-benzo[1,3]dioxol-5-ylmethyl)-piperazine-1-carboxylic acid (4-chloro-pyridin-3-yl)-amide compared favorably to Comparator Compound, which inhibited CYP2D6 with an $IC_{50}$ value of 3.2 µM using Bufuralol, and 2.0 µM using Dextromorphan as the test substrates. These results demonstrate an potential reduced risk of drug-drug interactions for 4-(2,2-difluoro-benzo[1,3]dioxol-5-ylmethyl)-piperazine-1-carboxylic acid (4-chloro-pyridin-3-yl)-amide relative to Comparator Compound.

TABLE 2

| Compound | 2D6 Bufuralol (µM) | 2D6 Dextromethorphan (µM) |
|---|---|---|
| Example 1 | 24 | 11 |
| Comparator Compound | 3.2 | 2.0 |

Primary Observation (Irwin) Test in the Rat 4-(2,2-Difluoro-benzo[1,3]dioxol-5-ylmethyl)-piperazine-1-carboxylic acid (4-chloro-pyridin-3-yl)-amide hydrochloride and the hydrochloride salt of Comparator Compound were investigated with oral administration in the Primary Observation (Irwin) Test in the rat to evaluate their general effects on behavior and physiological functions. The method, which detects the first toxic dose, the active dose-range and the main effects of a test substance on behavior and physiological function, follows that described by Irwin et al., *Psychopharmacologia*, 1968, 13, 222-257. The rats were administered the test substance and were observed in simultaneous comparison with a control group given vehicle (non-blind conditions). All animals within a treatment group were observed simultaneously. Behavioral modifications, physiological and neurotoxicity symptoms, rectal temperature and pupil diameter were recorded according to a standardized observation grid derived from that of Irwin. The grid contains the following items: death, convulsions, tremor, Straub tail, altered activity, jumping, abnormal gait (rolling, tip-toe), motor uncoordination, altered abdominal muscle tone, loss of grasping, akinesia, catalepsy, loss of traction, loss of balance, fore-paw treading, writhes, pilo-erection, stereotypies (sniffing, chewing, head movements), head twitches, scratching, altered respiration, aggression, altered fear/startle, altered reactivity to touch, ptosis, exophthalmia, loss of righting reflex, loss of corneal reflex, analgesia, defecation/diarrhea, salivation, lacrimation, rectal temperature (hypothermia/hyperthermia) and pupil diameter (myosis/mydriasis). The test substances were evaluated at 2 doses (10 and 60 mg/kg), administered p.o. immediately before the test, and compared with a vehicle control group. Observations were performed 15, 30, 60, 120 and 180 minutes after administration of the test substances/vehicles and also 24 hours later.

TABLE 3

| Example 1 (mg/kg p.o.) | | Comparator Compound HCl (mg/kg p.o.) | |
|---|---|---|---|
| 10 | 60 | 10 | 60 |
| Increased reactivity to touch: (1/4) at 180 min | Sedation: (0/4) Abnormal gait: (0/4) Hypothermia: (0/4) Increased abdominal muscle tone: (1/4) at 60 min Increased reactivity to touch: | Increased reactivity to touch (3/3) at 15 min | Sedation: (3/3) 15 to 120 min Abnormal gait (rolling): (3/3) at 15 min Hypothermia: slight induction at 15 to 60 min and at 180 min Decreased muscle tone: (1/3) at 30 min |

TABLE 3-continued

| Example 1 (mg/kg p.o.) | | Comparator Compound HCl (mg/kg p.o.) | |
|---|---|---|---|
| 10 | 60 | 10 | 60 |
| | (1/4) at 60 min<br>(1/4) at 180 min | | (3/3) at 60 to 120 min<br>Increased reactivity to touch:<br>(0/3) at 60 min and 180 min |

4-(2,2-difluoro-benzo[1,3]dioxol-5-ylmethyl)-piperazine-1-carboxylic acid (4-chloro-pyridin-3-yl)-amide hydrochloride caused weak and transient arousing effects in only one rat over the dose-range 10-60 mg/kg in the Irwin Test (Table 3). At 10 mg/kg, 4-(2,2-difluoro-benzo[1,3]dioxol-5-ylmethyl)-piperazine-1-carboxylic acid (4-chloro-pyridin-3-yl)-amide hydrochloride increased reactivity to touch in 1 out of 4 rats at 180 minutes. At 60 mg/kg, 4-(2,2-difluoro-benzo[1,3]dioxol-5-ylmethylypiperazine-1-carboxylic acid (4-chloro-pyridin-3-yl)-amide hydrochloride increased abdominal muscle tone in 1 out of 4 rats at 60 minutes and increased reactivity to touch in 1 out of the 4 rats at 60 and 180 minutes. Apart from transient and occasional increase in abdominal muscle tone at 60 mg/kg, no other signs were observed up to 24 hours after administration.

4-(2,2-difluoro-benzo[1,3]dioxol-5-ylmethyl)-piperazine-1-carboxylic acid (4-chloro-pyridin-3-yl)-amide hydrochloride showed favorable differentiation from Comparator Compound HCl in the Irwin Test at both doses. Whereas 4-(2,2-difluoro-benzo[1,3]dioxol-5-ylmethyl)-piperazine-1-carboxylic acid (4-chloro-pyridin-3-yl)-amide hydrochloride caused increased reactivity to touch in only 1 in 4 rats at 10 mg/kg, Comparator Compound HCl increased reactivity to touch in all 3 rats. At 60 mg/kg, Comparator Compound HCl induced sedation from 15 to 120 minutes and abnormal gait (rolling) at 15 minutes in all 3 rats. It decreased muscle tone in 1 rat at 30 minutes and from 60 to 120 minutes in all 3 rats. It also induced hypothermia from 15 to 60 minutes and at 180 minutes. These results suggest the presence of sedative/depressant effects (sedation, motor signs and hypothermia) for Comparator Compound HCl at 60 mg/kg p.o. that were not observed with 4-(2,2-difluoro-benzo[1,3]dioxol-5-ylmethyl)-piperazine-1-carboxylic acid (4-chloro-pyridin-3-yl)-amide hydrochloride.

What is claimed is:

1. A method of treating a patient suffering from a disorder selected from the group consisting of anxiety, depression and post-traumatic stress disorder comprising administering to said patient a therapeutically effective amount of 4-(2,2-difluoro-benzo[1,3]dioxol-5-ylmethyl)-piperazine-1-carboxylic acid (4-chloro-pyridin-3-yl)-amide or a pharmaceutically acceptable salt thereof.

2. A method according to claim 1, wherein the disorder is anxiety.

3. A method according to claim 1, wherein the disorder is depression.

4. A method according to claim 1, wherein the disorder is post-traumatic stress disorder.

5. A method of treating a patient suffering from a disorder selected from the group consisting of anxiety, depression and post-traumatic stress disorder comprising administering to said patient a pharmaceutical composition comprising a therapeutically effective amount of 4-(2,2-difluoro-benzo[1,3]dioxol-5-ylmethyl)-piperazine-1-carboxylic acid (4-chloro-pyridin-3-yl)-amide or a pharmaceutically acceptable salt thereof, and a pharmaceutically acceptable excipient.

6. A method according to claim 5, wherein the disorder is anxiety.

7. A method according to claim 5, wherein the disorder is depression.

8. A method according to claim 5, wherein the disorder is post-traumatic stress disorder.

9. A method according to claim 1 wherein the effective amount comprises 0.01 mg/kg per day to 35 mg/kg per day.

* * * * *